United States Patent [19]

Viso et al.

[11] Patent Number: 5,103,047
[45] Date of Patent: Apr. 7, 1992

[54] PROCESS FOR PREPARATION OF 4- AND 5-KETOCARBOXYLIC ACIDS

[75] Inventors: Miguel Viso, Greensboro; Jack R. Reid, Whitsett, both of N.C.

[73] Assignee: Lorillard Tobacco Company, New York, N.Y.

[21] Appl. No.: 516,251

[22] Filed: May 1, 1990

[51] Int. Cl.$^5$ ............................................. C07C 51/31
[52] U.S. Cl. ..................................... 562/524; 554/115
[58] Field of Search ......................... 562/524; 260/413

[56] References Cited

U.S. PATENT DOCUMENTS 2,759,005  8/1956  Starker et al. ...................... 260/413
3,412,116  11/1968  Reinheckel et al. ................. 260/413
3,654,326  4/1962  Rosenberger ....................... 260/413

*Primary Examiner*—Jose G. Dees
*Attorney, Agent, or Firm*—White & Case

[57] ABSTRACT

This invention is a novel synthesis of 4-and 5-ketocarboxylic acids which includes the reaction of the appropriate delta- or gamma-lactone with a chromosulfuric acid solution and separating the 4- or 5-ketocarboxylic acid product from the reduced solution.

5 Claims, No Drawings

PROCESS FOR PREPARATION OF 4- AND 5-KETOCARBOXYLIC ACIDS

BACKGROUND OF THE INVENTION

Ketocarboxylic acids which have the following general formula:

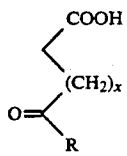

wherein R is an alkyl group and X is 1 or 2 have found wide utility as surfactants, British Patent 1,081,234, and as potential flavorants, British Patent 1,053,600, as well as serving as intermediates in the synthesis of more complex materials, such as steroids, Noland, W.F., Ed., "Organic Synthesis", Collective Volume 6, John Wiley & Sons, Inc. New York, 1988, p. 774, and Blickenstaff, R.T.; Ghosh, A.C.; Wolf, G.C.; "Total Synthesis of Steroids", Academic Press, New York, 1974.

In the past, ketocarboxylic acids have been prepared by a number of methods including the hydrolysis of acetylenic esters, Arcadi, A.; Cacchi, S.; Marinelli, F.; Misiti, D.; The Reaction of Alkyl 4-Hydroxy-2-alkynoates and 4-Hydroxy-2-alkyn-1-ones with Palladium Tributylammonium Formate and with Tributylamine: Preparation of 1,4-Dicarbonyl Compounds, Tetrahedron Letters, Volume 29, No. 12, pp. 1457-60, 1988; the reaction of a Grignard reagent upon furfural, followed by hydrolysis, Ponomarev, A.A.; Sedavkina, V.A.; Gamma-Oxoundecanoic Acid, Metody Poluch. Khim. Reakivov Prep. No. 17, pp. 59-62, 1967; and the reaction of a Grignard reagent upon the silyl derivatives of lactones, followed by hydrolysis, Betancourt de Perez, R. M.; Fuentes, L. M.; Larson, G. L.; Barnes, C. L.; Heeg, M. J.; A Synthesis of 4-Ox Carboxylic Acids, 4-Oxo Aldehydes and 1,4-Diketones from Gamma-Lactones, Journal of Organic Chemistry, Volume 51, No. 11, pp. 2039-43, 1986. More recently a wider range of synthetic techniques for preparing ketocarboxylic acids have been employed. These include methods such as the hydrolysis of an addition product of a nitroalkane on acrolein, Ballini, R.; Pertini, M.; Facile and Inexpensive Synthesis of 4-Oxoalkanoic Acids from Primary Nitroalkanes and Acrolein, Synthesis, pp. 1024-26, 1986, or the reaction of an alkyl lithium reagent on a lactone, followed by oxidation of the keto-alcohol, Fernandez, S.; Hernandez, J. E.; Cisneros, A.; Three Step Synthesis of Racemic Lactonic Pheromones, Rev. Latinoam Quim., Volume 16, No. 1, pp. 22-4, 1985.

A number of known syntheses specifically aimed at preparing the alpha ketocarboxylic acids involve the reactions of alkyl halides with carbon monoxide at elevated temperatures with the use of a special catalyst, U.S. Pat.No. 4,738,802; and the oxidation of a lactic acid or amide, followed by hydrolysis, U.S. Pat. Nos. 4,242,525, and 3,897,467.

More general reactions for the preparation of ketocarboxylic acids involve the use of alkyl aluminum compounds, German Patent 1,288,584, German Patent 51,309, Chemical Abstract 70: 77356y (1969); Grignard reagents with a succinic or glutaric anhydride, Japanese Patent 81/161,348; or the alkaline hydrolysis of dihaloacids, Japanese Patent 69/08,487, Chemical Abstract 71:90833s (1969). Ozone and chromium trioxide have also been used as oxidants for alpha, beta-unsaturated ketones or the corresponding alcohol acids, Japanese Patent 68/22,575, U.S. Pat. No. 4,612,391, U.S. Pat. No. 4,126,748, U.S. Pat. No. 2,848,480, U.S. Pat. No. 1,715,654, and U.S. Pat. No. 3,719,706.

The majority of these known prior art synthetic methods for ketocarboxylic acids involve multi-step reaction schemes followed by a difficult separation to sufficiently purify the ketocarboxylic acid product. It was the aim of this invention to develop a simple process to prepare 4- and 5-ketocarboxylic acids in an economical, one step procedure which would yield a ketocarboxylic acid devoid of unwanted by-products and require minimal separation techniques.

SUMMARY OF THE INVENTION

It has now been found that the synthesis of a 4- or 5-ketocarboxylic acid can be efficiently accomplished by a process which comprises the steps of subjecting a solution of the corresponding gamma- or delta-lactone to chromosulfuric acid oxidation and recovering the ketocarboxylic acid from the solution. This process is suitable for the oxidative preparation of 4- and 5-ketocarboxylic acids having the following formula (I),

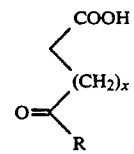

from the corresponding gamma- or delta-lactone having the following formula (II) .

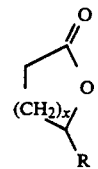

wherein R is an alkyl group having 1-20 carbon atoms and X is 1 or 2.

DETAILED DESCRIPTION OF THE INVENTION

The preferred process comprises the following steps (1) forming a reaction medium by dissolving an aliphatic delta- or gamma-lactone having formula II wherein R is an alkyl group having 1 to 20 carbon atoms and X is 1 or 2, in a suitable organic solvent in an amount of between 10-30 times the volume of the lactone (2) preparing an oxidation solution by dissolving about 4.5 equivalents of an oxidant, such as chromic (VI) oxide, sodium or potassium dichromate in twice the volume of water as the oxide or dichromate and adding an equal volume of 98% sulfuric acid to the oxidation solution and cooling the resulting solution to room temperature, 3) adding the cooled chromosulfuric acid oxidation solution dropwise with agitation to the dissolved lactone while holding the temperature of the reaction mixture between 40° C.-60° C. by suitable means as necessary, (4) destroying the excess oxidizing medium by the addition of a suitable alcohol, like 2- propanol, until the characteristic orange color has disappeared, (5) concentrating the mixture under reduced pressure, and combining the residue with 20-40 times its volume of water, (6) extracting the mixture portionwise with a suitable solvent, such as ether, chloroform, or dichloromethane, and (7) recovering the solid or liquid 4- or 5-ketocarboxylic acid from the extract by fractional distillation or crystallization.

The preferred organic solvent for dissolving the lactone is acetone, methyl ethyl ketone, or an acetone admixture with water, not exceeding 30% water by volume. Commercial grade aliphatic lactones may be used directly in this process without need of further purifications.

After the oxidizing solution has been completely added to the lactone, the reaction mixture can be processed immediately or stirred at room temperature for additional time, up to about 72 hours.

The recovery of the ketocarboxylic acid from the diluted concentrate can be performed by portionwise extraction or by any known continuous extraction technique. Suitable extraction solvents would include solvents similar to dichloromethane and ethyl acetate.

The oxidation solution can contain any suitable chromium compound, for example, chromic (VI) oxide, sodium dichromate, and potassium dichromate.

The invention will be more fully understood but not limited by reference to the following specific examples:

EXAMPLE 1

4-Oxoundecanoic Acid

Into a stirred solution of 80 ml of acetone and 5.9 grams of gamma-undecalactone a cooled solution (20°C.) made up of the following: 25 mL cold water, 13.4 grams of chromic (VI) oxide and 12 mL of 98% sulfuric acid was added dropwise. The internal temperature of the reaction mixture was held at 55° C. with ice bath cooling. At the end of the addition the ice bath was removed and the mixture was allowed to reach room temperature over a period of about 45 minutes. With continued stirring, 2-propanol was added slowly to the orange colored reaction mixture until the orange color was discharged. The mixture was concentrated by removal of the majority of the acetone under reduced pressure.

This concentrate was mixed with 250 mL of water and the mixture was then extracted with four 50 mL portions of ether, and the combined ether extracts were dried over anhydrous sodium sulfate. The extracts were filtered and the filtrate was concentrated to yield a white solid product. Recrystallization of the material from a minimum of hexane yielded 5.3 grams (83% yield) of white needle-like crystals, m.p. 78-78.5° C. A 1.0 gram portion of the starting lactone was recovered from the recrystallization mother liquors. 13C and 1H NMR and IR spectra confirmed the structure of the product. $v(cm-1)$ (C=O) 1740, C11H20O3 :calc : C 65.96, H: 10.07; Found: C 66.03, H: 10.04

EXAMPLE 2

5-Oxoundecanoic Acid

Using the procedure described in Example 1, 5.9 grams of delta-undecalactone were converted to 5.1 grams of 5-oxoundecanoic acid, mp 58-59° C., and 1.7 grams of unreacted starting material were recovered. 13C and 1H NMR and IR spectra confirmed the structure of the product. $v(cm-1)$ (C=O) 1740, Calc: C 65.96, H: 10.07; Found: C 65.80, H: 10.04

EXAMPLE 3

5-Oxodecanoic Acid

Using the procedure of Example 1, 5.5 grams of delta-decalactone were converted to 4.7 grams of 5-oxodecanoic acid, mp 54-55° C., and 0.5 grams of unreacted material were recovered. 13C and 1H NMR and IR spectra confirmed the structure of the product. $v(cm-1)$ (C=O) 1740, Calc: 64.48, H 9.74; Found: C 64.52, H: 9.75

EXAMPLE 4

4-Oxohexanoic Acid

Using the procedure of Example 1, 3.65 grams of gamma-caprolactone were converted to 3.15 grams of 4-oxohexanoic acid, bp 97-102° C. at 0.01mm. Upon standing the material solidified having a mp 36-37.5° C. 13C and 1H NMR and IR spectra confirmed the structure of the product. $v(cm-1)$ (C=O) 1721 Calc: C 55.37, H 7.75; Found : C 55.14, H 7.85

EXAMPLE 5

4-Oxononanoic Acid

Using the procedure of Example 1, 133.55 grams of gamma-nonalactone were converted to 117.8 grams, 80% yield, of 4-oxononanoic acid, mp 67-68° C. 13C and 1H NMR and IR spectra confirmed the structure of the product. $v(cm-1)$ (C=O) 1720 C9H16O3 Calc: C 62.77; H 9.36; Found: C 62.32, H 9.48

Other 4-and 5-ketocarboxylic acids as defined herein can be prepared from the corresponding gamma- or delta-lactone using this same process.

We claim:

1. A process for the preparation of a ketocarboxylic acid having the formula:

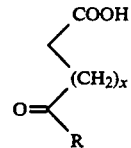

wherein R is an alkyl group having 1 t 20 carbon atoms and X is 1 or 2, comprising the steps of subjecting a solution of the corresponding lactone t oxidation using a solution containing a compound selected from the group consisting of chromic (VI) oxide, sodium dichromate and potassium dichromate admixed with an aqueous sulfuric acid solution while holding the temperature of the reaction mixture between 40°-60° C.

2. A process according to claim 1 wherein the ketocarboxylic acid is selected from the group consisting of a 4-ketocarboxylic acid and a 5-ketocarboxylic acid and the lactone is selected from the group consisting of a gamma alkyl lactone and a delta alkyl lactone.

3. Process according to claim 1 wherein the ketocarboxylic acid is selected from the group consisting of 4-oxoundecanoic acid, 5-oxoundecanoic acid, 5- oxodecanoic acid, 4-oxohexanoic acid and 4-oxononanoic acid.

4. A process for the preparation of a ketocarboxylic acid having the formula:

wherein R is an alkyl group having 1 to 20 carbon atoms and X is 1 or 2 comprising the steps of:

1) dissolving in an organic solvent a lactone having the formula:

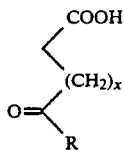

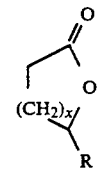

wherein R and X are as defined above;
2) preparing a colored oxidation solution by dissolving a compound selected from the group consisting of chromic (VI) oxide, sodium dichromate and potassium dichromate in water;
3) adding an equal volume of sulfuric acid to the oxidation solution
4) adding the resulting oxidation solution to the lactone, keeping the reaction mixture at about 40° C.–60° C.
5) adding an alcohol to the reaction mixture until the color disappears and
6) recovering the ketocarboxylic acid.

5. A process according to claim 2 wherein the lactone is dissolved in a solvent selected from the group consisting of acetone, methyl ethyl lactone and an acetone admixture not exceeding 30% water by volume.

* * * * *